United States Patent
McDaniel et al.

(10) Patent No.: US 8,882,705 B2
(45) Date of Patent: *Nov. 11, 2014

(54) STEERABLE CATHETER WITH IN-PLANE DEFLECTION

(75) Inventors: Benjamin D. McDaniel, Irvine, CA (US); Thomas V. Selkee, Claremont, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 219 days.

This patent is subject to a terminal disclaimer.

(21) Appl. No.: 13/110,725

(22) Filed: May 18, 2011

(65) Prior Publication Data

US 2011/0218492 A1 Sep. 8, 2011

Related U.S. Application Data

(63) Continuation of application No. 11/058,102, filed on Feb. 14, 2005, now Pat. No. 7,959,601.

(51) Int. Cl.
*A61M 31/00* (2006.01)

(52) U.S. Cl.
USPC ...................................................... 604/95.04

(58) Field of Classification Search
USPC ....................................... 604/95.04; 600/139
See application file for complete search history.

(56) References Cited

U.S. PATENT DOCUMENTS

| 2,498,692 A | 2/1950 | Mains |
| 3,371,573 A | 3/1968 | Koreki et al. |

(Continued)

FOREIGN PATENT DOCUMENTS

| EP | 0 689 851 A1 | 1/1996 |
| EP | 1 120 082 A | 8/2001 |

(Continued)

OTHER PUBLICATIONS

European Search Report dated Jun. 9, 2006, for European Application No. 06250723.1, in the name of Biosense Webster, completed May 15, 2006, 14 pgs.

(Continued)

*Primary Examiner* — Nicholas Lucchesi
*Assistant Examiner* — Pritesh Patel
(74) *Attorney, Agent, or Firm* — Christie, Parker & Hale, LLP (57) ABSTRACT

An improved steerable catheter with in-plane deflection comprises a catheter body having proximal and distal ends and a lumen extending therethrough and a tip section at the distal end of the catheter body. The tip section comprises a flexible plastic tubing having a pair of diametrically-opposed lumens extending therethrough. The catheter also provides two puller wires manipulated through a control handle at the proximal end of the catheter body. Each puller wire extends through one of the pair of lumens in the tip section and through the lumen of the catheter body and is anchored to the control handle at its proximal end and anchored to the tip section at its distal end. The deflection mechanism is configured to generally define a plane along which deflection most readily occurs and an edge along which deflection is most readily avoided. The deflection mechanism extends longitudinally along a centerline of the tip section between the first and second puller wire and is configured generally with a cross section having a thinner dimension and a thicker dimension to bias the tip section to deflect in a plane parallel with the thinner dimension of the deflection mechanism and to resist deflection in a plane perpendicular to thicker dimension.

15 Claims, 10 Drawing Sheets

(56) References Cited

U.S. PATENT DOCUMENTS

| | | | |
|---|---|---|---|
| 3,470,876 | A | 10/1969 | Barchilon |
| 3,783,736 | A | 1/1974 | Richardson |
| 4,619,643 | A | 10/1986 | Bai |
| 4,686,963 | A | 8/1987 | Cohen et al. |
| 5,195,968 | A * | 3/1993 | Lundquist et al. ......... 604/95.04 |
| 5,199,950 | A | 4/1993 | Schmitt et al. |
| 5,254,088 | A | 10/1993 | Lundquist et al. |
| 5,257,571 | A | 11/1993 | Richardson |
| RE34,502 | E | 1/1994 | Webster, Jr. |
| 5,318,525 | A | 6/1994 | West et al. |
| 5,374,245 | A | 12/1994 | Mahurkar |
| 5,391,199 | A | 2/1995 | Ben-Haim |
| 5,395,327 | A | 3/1995 | Lundquist et al. |
| 5,395,328 | A | 3/1995 | Ockuly et al. |
| 5,443,489 | A | 8/1995 | Ben-Haim |
| 5,456,674 | A | 10/1995 | Bos et al. |
| 5,480,422 | A | 1/1996 | Ben-Haim |
| 5,500,012 | A | 3/1996 | Brucker et al. |
| 5,507,725 | A | 4/1996 | Savage et al. |
| 5,545,200 | A | 8/1996 | West et al. |
| 5,546,951 | A | 8/1996 | Ben-Haim |
| 5,558,091 | A | 9/1996 | Acker et al. |
| 5,568,809 | A | 10/1996 | Ben-Haim |
| 5,674,197 | A | 10/1997 | van Muiden et al. |
| 5,676,653 | A | 10/1997 | Taylor et al. |
| 5,715,817 | A | 2/1998 | Stevens-Wright et al. |
| 5,820,591 | A | 10/1998 | Thompson et al. |
| 5,824,031 | A | 10/1998 | Cookston et al. |
| 5,855,560 | A | 1/1999 | Idaomi et al. |
| 5,897,529 | A | 4/1999 | Ponzi |
| 5,906,590 | A | 5/1999 | Hunjan et al. |
| 5,964,757 | A | 10/1999 | Ponzi |
| 6,064,908 | A | 5/2000 | Muller et al. |
| 6,123,699 | A | 9/2000 | Webster, Jr. |
| 6,171,277 | B1 * | 1/2001 | Ponzi ........................ 604/95.04 |
| 6,183,463 | B1 | 2/2001 | Webster, Jr. |
| 6,198,974 | B1 | 3/2001 | Webster, Jr. |
| 6,201,387 | B1 | 3/2001 | Govari |
| 6,210,407 | B1 | 4/2001 | Webster |
| 6,267,746 | B1 | 7/2001 | Bumbalough |
| 6,402,719 | B1 * | 6/2002 | Ponzi et al. ................ 604/95.04 |
| 6,450,948 | B1 | 9/2002 | Matsuura et al. |
| 6,522,933 | B2 | 2/2003 | Nguyen |
| 6,569,114 | B2 | 5/2003 | Ponzi et al. |
| 6,602,242 | B1 | 8/2003 | Fung et al. |
| 6,913,594 | B2 | 7/2005 | Coleman et al. |
| 7,018,372 | B2 | 3/2006 | Casey et al. |
| 7,377,906 | B2 | 5/2008 | Selkee |
| 8,182,467 | B2 | 5/2012 | Nguyen et al. |
| 8,376,991 | B2 | 2/2013 | Kauphusman et al. |
| 2002/0161353 | A1 | 10/2002 | Kortelling |
| 2003/0004493 | A1 | 1/2003 | Casey et al. |
| 2003/0045831 | A1 | 3/2003 | Ponzi et al. |
| 2006/0135961 | A1 | 6/2006 | Rosenman et al. |
| 2006/0184106 | A1 | 8/2006 | McDaniel et al. |
| 2006/0184107 | A1 | 8/2006 | Bencini et al. |
| 2007/0010786 | A1 | 1/2007 | Casey et al. |
| 2007/0299424 | A1 | 12/2007 | Cumming et al. |
| 2008/0091169 | A1 | 4/2008 | Heideman et al. |
| 2008/0139999 | A1 | 6/2008 | Gibson et al. |
| 2008/0161762 | A1 | 7/2008 | Stehr et al. |
| 2009/0312698 | A1 | 12/2009 | Farrell et al. |
| 2012/0130218 | A1 | 5/2012 | Kauphusman et al. |
| 2012/0184901 | A1 | 7/2012 | Nguyen et al. |
| 2012/0203169 | A1 | 8/2012 | Tegg |
| 2012/0209073 | A1 | 8/2012 | McWeeney et al. |
| 2012/0277671 | A1 | 11/2012 | Fuentes |
| 2013/0030363 | A1 | 1/2013 | Wong et al. |

FOREIGN PATENT DOCUMENTS

| | | |
|---|---|---|
| EP | 1 690 564 A1 | 8/2006 |
| EP | 1 723 981 A1 | 11/2006 |
| JP | 07-213618 | 8/1995 |
| WO | WO 2005/113057 A1 | 12/2005 |

OTHER PUBLICATIONS

European Search Report dated Jan. 21, 2011 (search completed Jan. 11, 2011) for EP Application No. 10251664.8, 13 pages.

Extended European Search Report completed Nov. 20, 2012 and mailed Nov. 29, 2012 for EP Application No. 12189612.0 (15 pages).

English translation of JP Office action dated Nov. 29, 2012 issued in JP Application No. 2006-035418 (3 pages).

* cited by examiner

STEERABLE CATHETER WITH IN-PLANE DEFLECTION

CROSS REFERENCE TO RELATED APPLICATION(S)

This application is a continuation of U.S. patent application Ser. No. 11/058,102, filed Feb. 14, 2005 now U.S. Pat. No. 7,959,601, entitled "Steerable Catheter with In-Plane Deflection," the entire contents of which are incorporated herein by reference.

FIELD OF INVENTION

The present invention relates to an improved steerable catheter, in particular, a bi-directional catheter with in-plane deflection.

BACKGROUND OF INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable (or deflectable) catheters are generally well-known. For example, U.S. Pat. No. Re. 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the catheter tip section.

Often it is desirable to have a bidirectional steerable catheter, i.e., a catheter that can be deflected in two directions, typically opposing directions. For example, U.S. Pat. No. 6,210,407 discloses a bidirectional steerable catheter having two puller wires extending through the catheter. The distal ends of the puller wires are anchored to opposite sides of the tip section of the catheter. A suitable bidirectional control handle is provided that permits longitudinal movement of each puller wire to thereby allow deflection of the catheter in two opposing directions.

Regardless of whether the catheter is unidirectional or bidirectional, it is typically preferred that the tip section can be deflected in the plane of the catheter so that the catheter can be more precisely controlled in the heart. However, because the tip section is generally made of a flexible material, it is sometimes difficult to limit out-of-plane deflection. Accordingly, a need exists for a catheter having a tip section that can be consistently deflected within the plane of the catheter.

SUMMARY OF THE INVENTION

The present invention is directed to an improved steerable catheter having a deflection mechanism to provide a tip section with in-plane deflection. The deflection mechanism is elongated to extend longitudinally along the tip section and has a cross section that provides a lesser area moment of inertia about a first centroidal axis and a greater area moment of inertia about a second centroidal axis generally orthogonal to the first centroidal axis. As such, the deflection mechanism biases the tip section to deflect in a plane extending in the second centroidal axis with the greater area moment of inertia and resist deflection in a plane extending in the first centroidal axis with the lesser area moment of inertia.

The deflection mechanism can have a cross-section of any configuration, provided the cross-section provides two generally orthogonal centroidal axes with unequal area moments of inertia. As such, the deflection mechanism biases the tip section to deflect in a plane parallel with the centroidal axis with the greater area moment of inertia and resists flexion in a plane parallel with the centroidal axis with the lesser area moment of inertia.

In one embodiment, the deflection mechanism comprises one deflection member having a generally rectangular cross section with a width W along an x axis and a thinness T along a y axis, wherein the area moment of inertia along the x axis $I_x$ and the area moment of inertia along the y axis $I_y$ are defined as follows:

$$I_x = \frac{(W)T^3}{12}$$

$$I_y = \frac{(T)W^3}{12}$$

where $W=nT$, with n ranging between about 2 and 20, and preferably, between about 10 and 15, and more preferably with n being about 12. Accordingly, the deflection mechanism biases the tip section to deflect in a plane parallel with the y axis and resist deflection in a plane parallel with the x axis.

In an alternative embodiment, the deflection mechanism comprises a plurality of deflection members, each of which contributes to an effective or combined area moment of inertia along an x axis and an effective or combined area moment of inertia along a y axis, which biases the tip section to deflect in a plane parallel with the centroidal axis with the greater effective area moment of inertia and resist deflection in a plane parallel with the centroidal axis with the lesser effective area moment of inertia.

In a detailed embodiment, a catheter with in-plane deflection comprises a catheter body having proximal and distal ends and a lumen extending therethrough and a tip section at the distal end of the catheter body. The tip section comprises a flexible plastic tubing having a pair of diametrically-opposed lumens extending therethrough. The catheter also provides two puller wires manipulated through a control handle at the proximal end of the catheter body. The deflection mechanism is configured with a lesser area moment of inertia about a first centroidal axis and a greater area moment of inertia about a second centroidal axis generally orthogonal to the first centroidal axis so as to bias deflection of the tip section in a plane parallel with the second centroidal axis with the greater area moment of inertia and resist deflection in a plane parallel with the first centroidal axis with the lesser area moment of inertia.

In a more detailed embodiment, a catheter with in-plane deflection has a deflection mechanism comprising a single elongated deflection member positioned between the puller wires, the deflection member having a cross-section with a thicker dimension and a thinner dimension so as to bias a tip section to deflect in a plane parallel with the thinner dimension and resist deflection in a plane parallel with the thicker dimension.

In another more detailed embodiment, a catheter with in-plane deflection has a deflection mechanism comprising a plurality of elongated deflection members that are configured to provide a lesser effective or combined area moment of inertia about a first centroidal axis and a greater effective or combined area moment of inertia along a second centroidal axis. The deflection members jointly bias the tip section of the catheter to deflect in a plane parallel with the second centroidal axis and to resist deflection in a plane parallel with the first centroidal axis

DETAILED DESCRIPTION OF THE INVENTION

Figure 1:
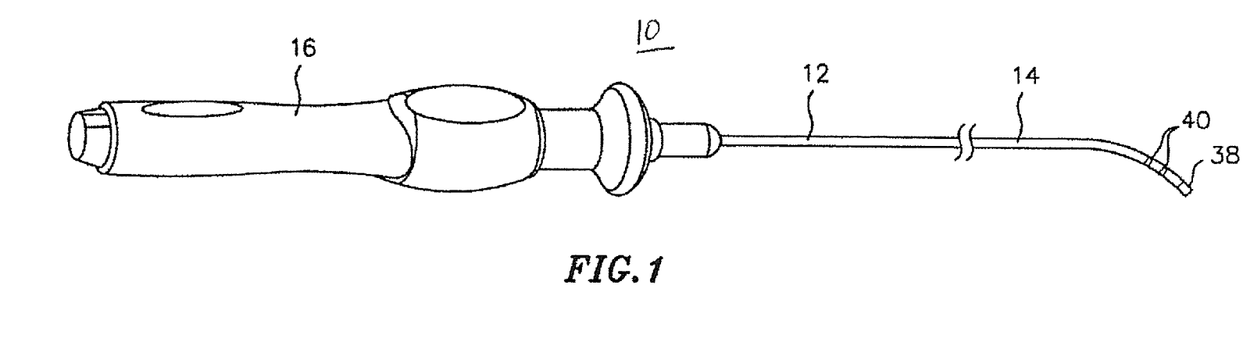
FIG. 1 is a side view of an embodiment of the catheter of the invention.

In an embodiment of the invention, there is provided a steerable bidirectional electrode catheter. As shown in FIG. 1, the catheter 10 comprises an elongated catheter body 12 having proximal and distal ends, a tip section 14 at the distal end of the catheter body 12, and a control handle 16 at the proximal end of the catheter body 12.

Figure 2:
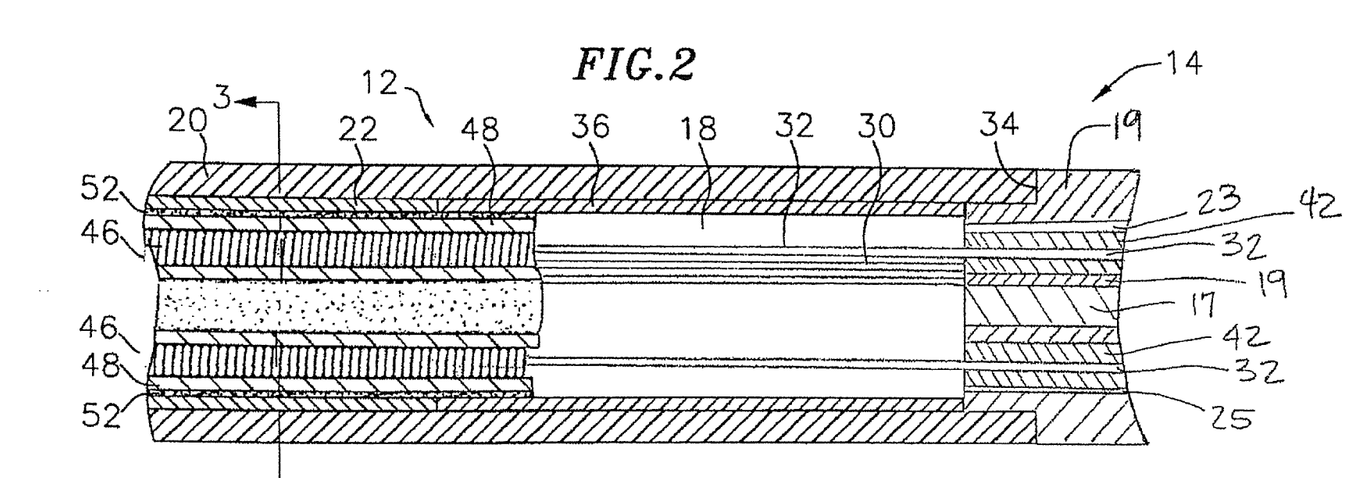
FIG. 2 is a side cross-sectional view of the junction of the catheter body and tip section of an embodiment of the catheter according to the invention.
Figure 3:
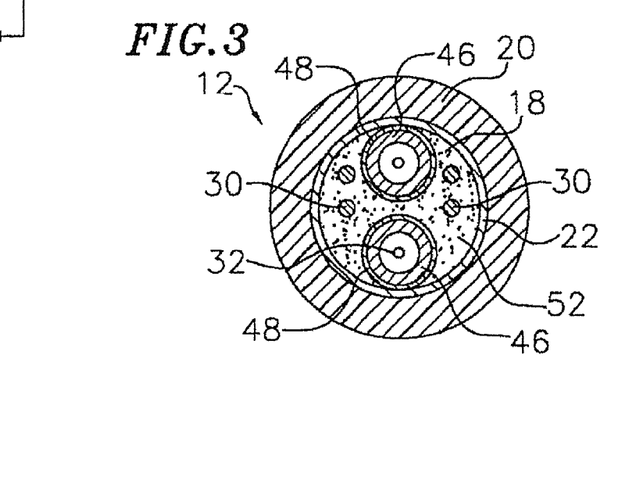
FIG. 3 is a traverse cross-sectional view of catheter body shown in FIG. 2 taken along line 3-3.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 8 french. The inner surface of the outer wall 20 is preferably lined with a stiffening tube 22, which can be made of any suitable material, preferably nylon or polyimide. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch. If desired, the stiffening tube can be omitted.

Figure 3A:
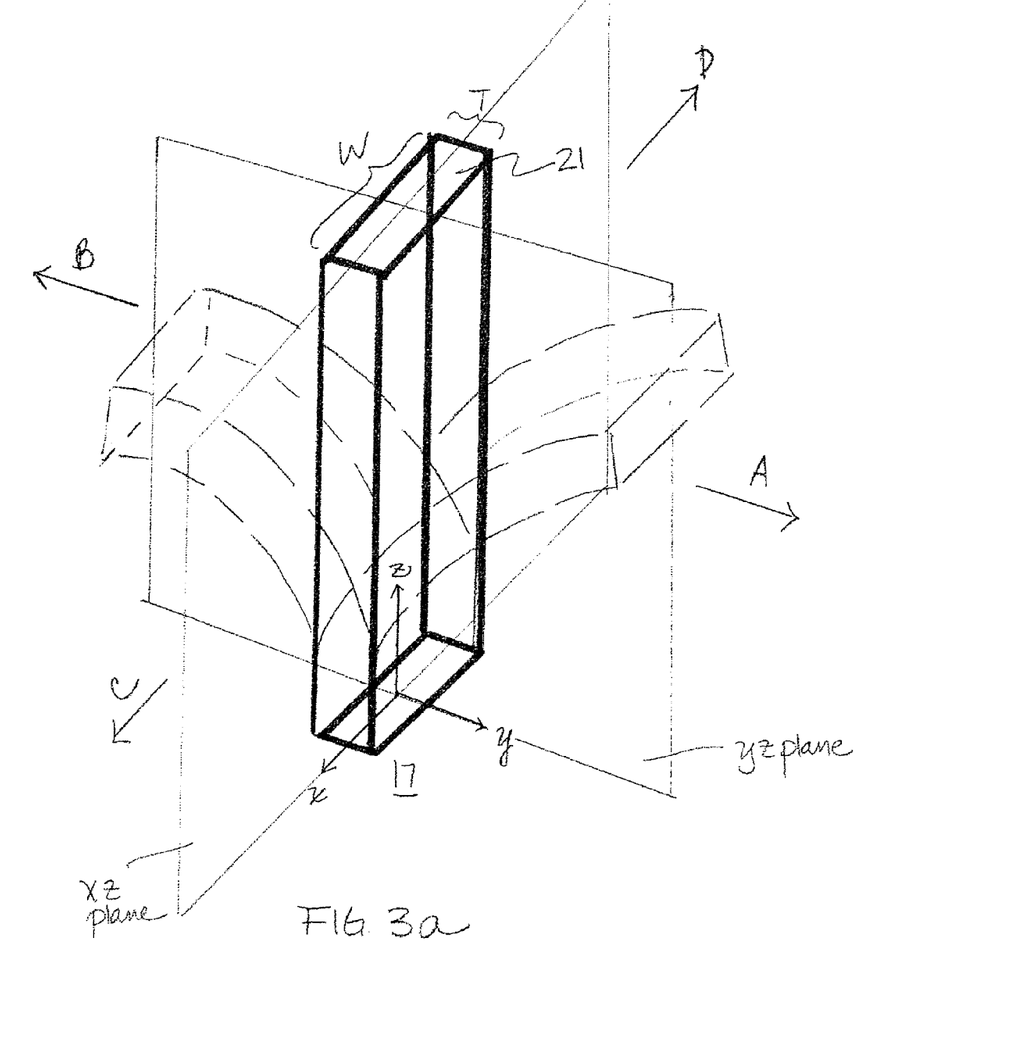
FIG. 3a is a view of an embodiment of the deflection mechanism with bi-directional deflection in a plane parallel with a Y axis (namely, a YZ plane) with a greater area moment of inertia $I_y$ and resisting bi-directional deflection in a plane parallel with an X axis (namely, an XZ plane) with a lesser area moment of inertia $I_x$.

The tip section 14 comprises a short section of flexible tubing 19 with a deflection structure 17 to bias the tip section for in-plane deflection. As illustrated in FIG. 3a, the deflection mechanism exhibits a tendency to flex in directions A and B along a y centroidal axis and resist flexure in directions C and D along an x centroidal axis. The deflection mechanism is elongated (e.g., along a z axis) and has a cross section 21 with a thinner dimension T extending along the y centroidal axis and a thicker dimension W along the x centroidal axis. The deflection mechanism therefore provides a lesser area moment of inertia about the x centroidal axis $I_x$ and a greater area moment of inertia about the y centroidal axis $I_y$, as defined by the following equations:

$$I_x = \frac{(W)T^3}{12}$$

$$I_y = \frac{(T)W^3}{12}$$

where W=nT with n ranging between about 2 to 20, preferably between about 10-15 and more preferably with n being about 12. As such, the deflection mechanism 17 tends to flex in a direction or plane parallel with a Y centroidal axis (namely, a YZ plane) and resist flexure in a direction or plane parallel with an X centroidal axis (namely, a XZ plane). Thus, the deflection mechanism provides "in-plane" bi-directional deflection, that is, bi-directional deflection in a plane parallel or aligned with the centroidal axis of the greater area moment of inertia, and resistance to "off-plane" bi-directional deflection in a plane parallel or aligned with the centroidal axis of the lesser area moment of inertia.

In the illustrated embodiment, the elongated deflection mechanism 17 has a generally rectangular cross section with a greater surface area extending in an XZ plane in comparison to a lesser surface area extending in a YZ plane. Accordingly, the in-plane deflection of this embodiment of the mechanism 17 can also be described as a deflection in a plane (namely, a YZ plane in FIG. 3a) that is generally orthogonal to the greater surface area of the deflection mechanism (namely, an XZ plane in FIG. 3a).

It is understood by one of ordinary skill in the art that the cross-section need not be rectangular but may be ovalized, or rather any configuration so long as there is an effective or combined thicker dimension and an effective or combined thinner dimension such that the area moments of inertia about the two centroidal axes are unequal, in particular, such that the effective or combined area moment of inertia about one centroidal axis is lesser than the effective or combined area moment of inertia about another centroidal axis generally orthogonal to the first centroidal axis.

Figure 4:
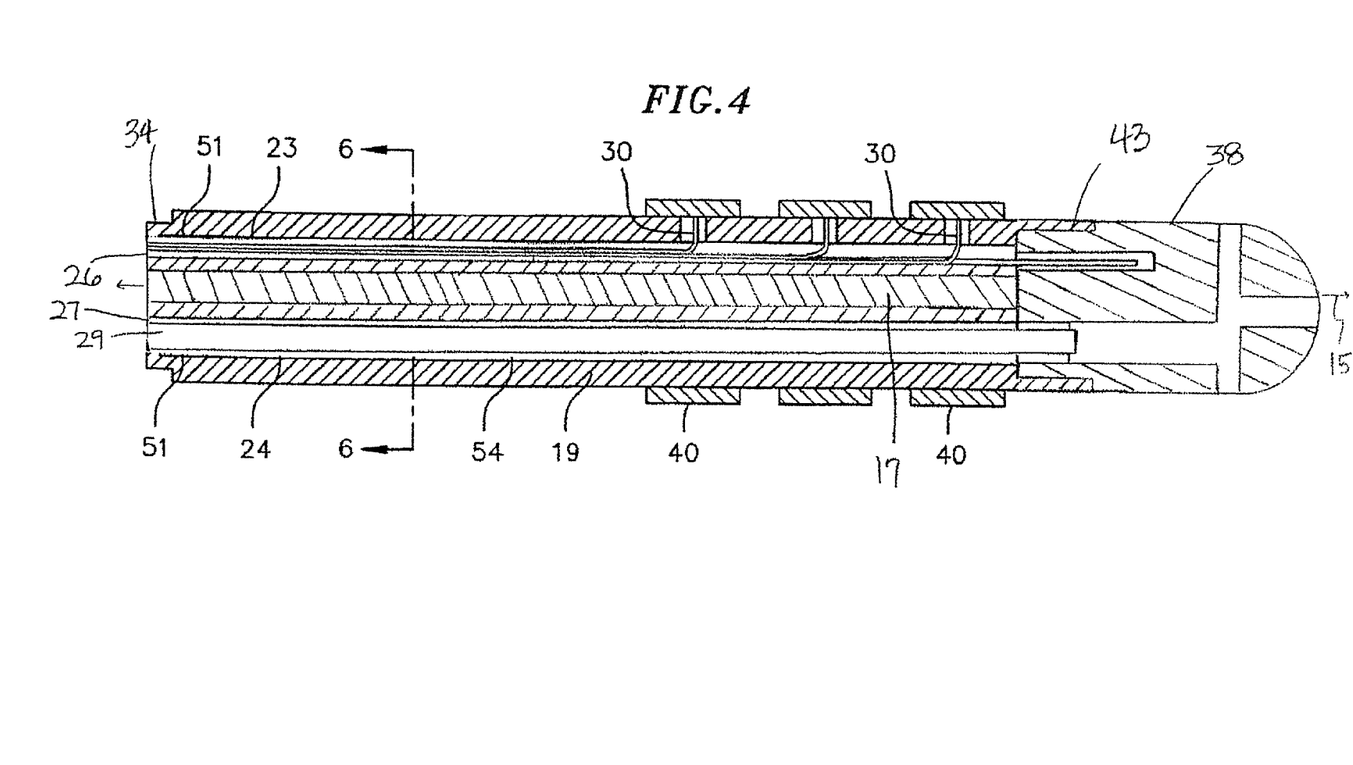
FIG. 4 is a side cross-sectional view of the tip section of an embodiment of the catheter of the invention showing the width dimension of the deflection mechanism and lumens carrying an infusion tube and lead wires.
Figure 5:
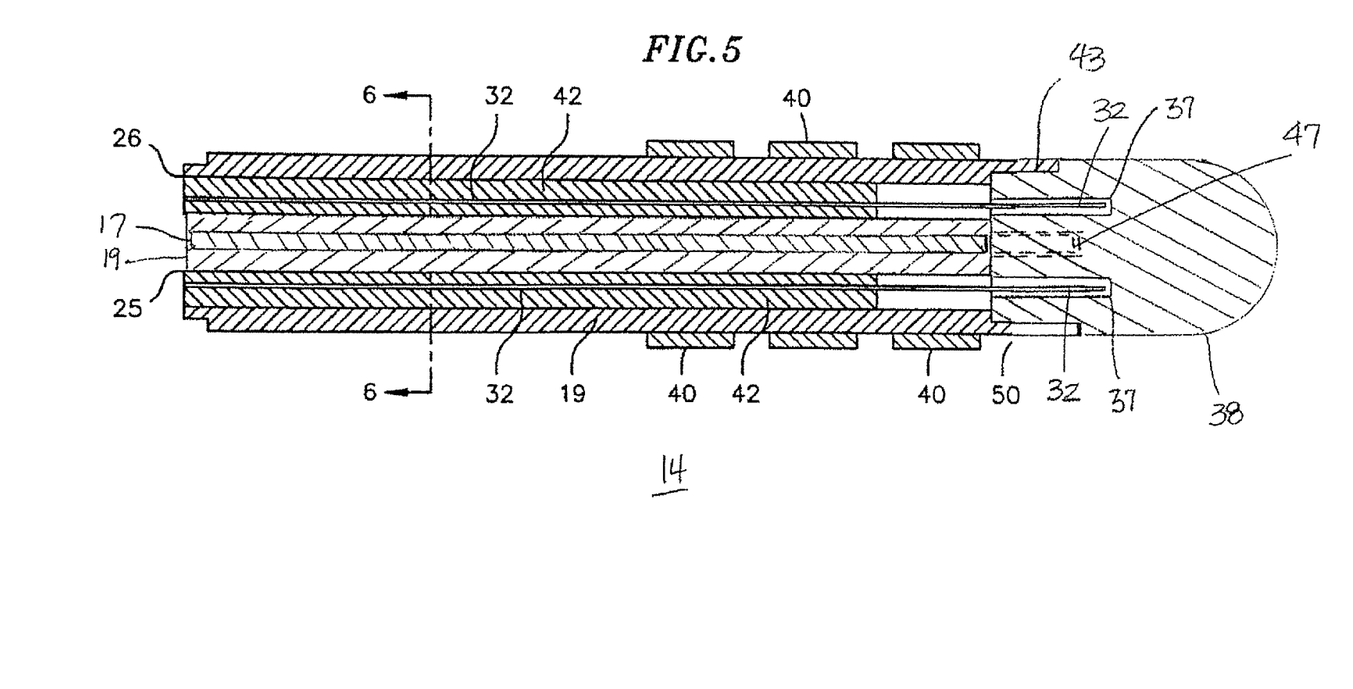
FIG. 5 is a side cross-sectional view of the tip section of an embodiment of the catheter of the invention showing the thickness dimension of the deflection mechanism and lumens carrying puller wires.
Figure 6:
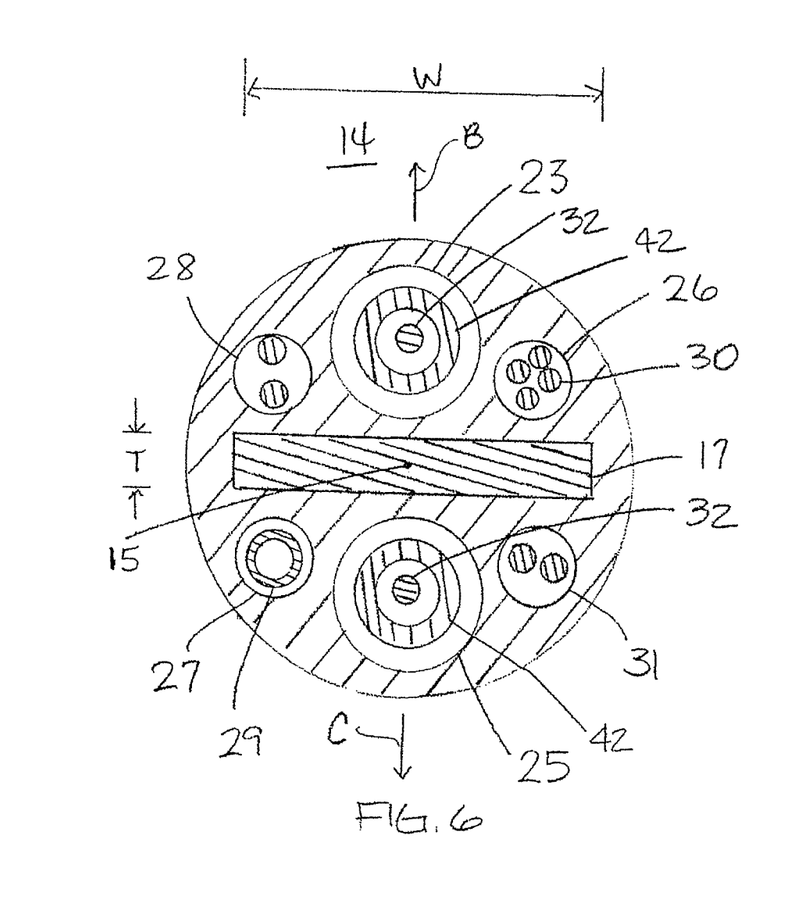
FIG. 6 is a traverse cross-sectional view of the tip section shown in FIG. 5 taken along line 6-6.

In the illustrated embodiment of FIGS. 4, 5 and 6, the deflection mechanism 17 comprises a planar strip that extends longitudinally along a neutral bending axis or centerline 15 of tubing 19 to promote maximum planar stability. The strip can be an elongated flat wire or sheet wire made of metal, plastic, ceramic or glass that is flexible with shape memory and/or superelastic properties. Preferably, the material should have a high percentage of strain before the material yields. Some suitable materials for the deflection mechanism include stainless steel, Nitinol, and metastable titanium-molybdenum base alloy. In a preferred embodiment, the strip has a generally uniform rectangular cross-section (FIG. 6) along its length. A suitable wire may have W about 0.070 inch and T about 0.005 inch, where n is about 14. The strip naturally exhibits a tendency to bend in-plane, that is, to flex readily along its thinner dimension and resist flexure along its thicker dimension.

The tubing 19 provides multiple off-axis lumens, including lumens 23 and 25 arranged diametrically opposed to each other across the deflection mechanism 17. Each of the lumens 23 and 25 carries a puller wire 32 for deflecting the tip section, as discussed further below. The tubing also provides a third off-axis lumen 26 to carry lead wires 30 for the electrodes of the tip section 14. The precise size of the lumens is not critical and will depend on the sizes of the components being carried by the lumens. As would be recognized by one skilled in the art, additional off-axis lumens could be provided if desired. For example, as shown in FIG. 6, a lumen 27 carrying a tube segment 29 could be provided for infusion of fluids out the distal end of the tip section and/or lumens 28 and 31 to carry additional wires and cables such as for a temperature sensor and/or navigation sensor provided in the tip section.

The flexible tubing 19 can comprise a single unitary piece of plastic or can comprise a series of layers, as is generally known in the art. For example, the flexible tubing 19 can comprise a plastic core, an inner plastic layer surrounding the core, a braided stainless steel mesh surrounding the inner layer, and an outer plastic layer surrounding the braided mesh. The core is preferably made by extruding the plastic over the deflection mechanism 17 and mandrels that are later removed to form the off-axis lumens. It is understood by one of ordinary skill in the art that the deflection mechanism 17 can also be incorporated into the tubing 19 by injection molding and/or fusing together of a collection of extruded, and molded components such that the tubing 19 and the deflection mechanism 17 are intimately bonded, fused, formed, melted and/or mechanically attached such that they generally act as a single unit with a built-in bias to deflect in a predetermined manner.

Over the core, the inner layer is formed by any suitable technique, such as extrusion, which can be performed simultaneously with the extrusion of the core. Thereafter, the braided mesh is formed over the inner layer. The braided mesh comprises interwoven helical members, typically twelve, sixteen or twenty-four interwoven helical members, half extending in one direction and the other half extending in the in the counter direction. The tightness or braid angle of the helical members to a line parallel with the axis of the catheter and intersecting the helical members is not critical, but is preferably about 45 degrees. The helical members are preferably made of a conductive material having a high modulus of elasticity. Preferred helical members are made of stainless steel wire. Other methods for forming a braided mesh known in the art may be used. Finally the outer layer is formed over the braided mesh by any suitable technique, preferably extrusion.

As would be recognized by one skilled in the art, the specific number and composition of the layers of the tip section 14 is not critical. For example, the inner layer can be omitted, particularly if it is desired to have a relatively small diameter tip section. The braided mesh can also be omitted, in which case the tip section 14 can optionally comprise a unitary core formed without additional plastic layers.

The tip section 14 is generally more flexible than the catheter body 12. The outer diameter of the tip section 14, like that of the catheter body 12, is preferably no greater than about 8 french, more preferably about 6½ french or less, but can vary depending on the particular application for which the catheter is to be used.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first tack-type glue joint (not shown) is made between the stiffening tube 22 and the outer wall 20 by a fast drying glue, e.g. Super Glue®. Thereafter a second glue joint is formed between the proximal ends of the stiffening tube 22 and outer wall 20 using a slower drying but more permanent glue, e.g., polyurethane. Other suitable techniques for attaching the catheter body 12 and tip section 14 can also be used in accordance with the present invention.

FIG. 4 provides a schematic side cross-sectional view of the tip section 14. The distal end of the tip section 14 carries a tip electrode 38. Mounted along the length of the tip section 14 are three ring electrodes 40. The length of each ring electrode 40 is not critical, but preferably ranges from about 1 mm to about 3 mm. The distance between the ring electrodes 40 is not critical so long as their edges do not touch. More or less ring electrodes 40 can be provided if desired.

The tip electrode 38 and ring electrode 40 are each connected to a separate electrode lead wire 30. The lead wires 30 extend through the lumen 26 in the tip section 14, through the central lumen 18 in the catheter body 12 and through the control handle 16. The proximal end of each lead wire 30 extends out the proximal end of the control handle 16 and is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by solder or the like, as shown in FIG. 4. Connection of a lead wire 30 to a ring electrode 40 is preferably accomplished by first making a small hole through the wall of the tip section 14 into the lumen 26 through which the lead wire extends, as also shown in FIG. 4. Such a hole can be created, for example, by inserting a needle through the wall of the tip section 14 and heating the needle sufficiently to form a permanent hole. A lead wire 30 is then drawn through the hole by using a microhook or the like. The end of the lead wire 30 is then stripped of any coating and welded to the underside of the ring electrode 40, which is then slid into position over the hole and fixed in place with polyurethane glue or the like. The tip electrode 38 receives the distal end of its lead wire in a blind hole 31. The distal end is soldered or welded to the tip electrode in the blind hole.

The two puller wires 32 extend through the catheter 10. Each puller wire 32 extends from the control handle 16, through the central lumen 18 in the catheter body 12 and into one of the off-axis lumens 23 and 25 of the tip section 14, as shown in FIG. 5. As described in more detail below, the proximal end of each puller wire 32 is anchored within the control handle 16, and the distal end of each puller wire 32 is anchored within the tip section 14.

Each puller wire 32 is made of any suitable material, such as stainless steel or Nitinol. Preferably each puller wire 32 has a coating, such as a coating of Teflon® or the like. Each puller wire 32 has a diameter preferably ranging from about 0.006 inch to about 0.0010 inch. Preferably both of the puller wires 32 have the same diameter.

Each puller wire 32 is anchored at or near the distal end of the tip section 14. In the embodiment depicted in FIG. 5, the puller wires 32 are both anchored in blind holes 37 in the tip electrode 38 by a welding or the like. Alternatively, one or both puller wires 32 can be anchored to the side wall of the tip section 14, as described in U.S. patent application Ser. No. 09/710,210, filed Nov. 10, 2000, the entire disclosure of which is incorporated herein by reference. Other means for anchoring the puller wires 32 in the tip section 14 would be recognized by those skilled in the art and are included within the scope of the invention.

In the depicted embodiment, the distal ends of the puller wires 32 are attached to opposite sides of the tip section 14. This design permits deflection of the tip section 14 in opposing directions (see arrows B and C in FIGS. 3a and 6).

The catheter further comprises two compression coils 46, each in surrounding relation to a corresponding puller wire 32 in the catheter body 12, as shown in FIGS. 2 and 3. Each compression coil 46 is made of any suitable metal, such as stainless steel. Each compression coil 46 is tightly wound on itself to provide flexibility, i.e., bending, but to resist compression. The inner diameter of each compression coil 46 is slightly larger than the diameter of its associated puller wire 32. For example, when a puller wire 32 has a diameter of about 0.007 inch, the corresponding compression coil 46 preferably has an inner diameter of about 0.008 inch. The coating on the puller wires 32 allows them to slide freely within the compression coil 46. The outer surface of each compression coil 46 is covered along most of its length by a flexible, non-conductive sheath 48 to prevent contact between the compression coil 46 and the lead wires 30 within the central lumen 18. The non-conductive sheath 48 made of thin-walled polyimide tubing is presently preferred.

At or near the distal end of the catheter body 12, the two compression coils 46 are positioned in diametric opposition within the stiffening tube 22 so that they can be aligned with the two off-axis lumens 23 and 25 in the tip section 14 through which the puller wires 32 extend. The compression coils 46 and stiffening tube 22 are sized so that the compression coils 46 fit closely and slidably within the stiffening tube 22. With this design, the lead wires 30 distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by a glue joint (not shown). When a stiffening tube 22 is not used, each compression coil is anchored directly to the outer wall 20 of the catheter body 12.

The distal end of each compression coil 46 is anchored to the distal end of the stiffening tube 22 in the catheter body 12 by a glue joint 52, or directly to the distal end of the outer wall 20 of the catheter body 12 when no stiffening tube 22 is used. Alternatively, the distal ends of the compression coils 46 may extend into the off-axis lumens 23 and 25 of the tip section 14 and are anchored at their distal ends to the proximal end of the tip section 14 by a glue joint. In the depicted embodiment, where the compression coils 46 are each surrounded by a sheath 48, care should be taken to insure that the sheath is reliably glued to the compression coil. The lead wires 30 can also be anchored in the glue joint. However, if desired, tunnels in the form of plastic tubing or the like can be provided around the lead wires at the glue joint to permit the lead wires to be slidable within the glue joint.

The glue joints preferably comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 20 and the stiffening tube 22 that is heated sufficiently to form a permanent hole. The glue is then introduced through the hole to the outer surface of the compression coil 46 and wicks around the outer circumference to form a glue joint about the entire circumference of each sheath 48 surrounding each compression coil 46. Care must be taken to insure that glue does not wick over the end of the coil so that the puller wire cannot slide within the coil.

As shown in FIG. 5, within the off-axis lumens 23 and 25, each puller wire 32 is surrounded by a plastic sheath 42, preferably made of Teflon®. The plastic sheaths 42 prevent the puller wires 32 from cutting into the wall of the tip section 14 when the tip section is deflected. Each sheath 42 ends near the distal end of each puller wire 32. Alternatively, each puller wire 32 can be surrounded by a compression coil where the turns are expanded longitudinally, relative to the compression coils extending through the catheter body, such that the surrounding compression coil is both bendable and compressible.

Longitudinal movement of a puller wire 32 relative to the catheter body 12, which results in deflection of the tip section 14 in the direction of the side of the tip section to which that puller wire is anchored, is accomplished by suitable manipulation of the control handle 16. A suitable bidirectional control handle for use in the present invention is described in U.S. application Ser. No. 09/822,087, filed Mar. 30, 2001 and entitled "Steerable Catheter with a Control Handle Having a Pulley Structure", the entire disclosure of which is incorporated herein by reference. Other suitable bidirectional control handles are described in U.S. Pat. Nos. 6,123,699; 6,171,277; 6,183,463; and 6,198,974, the entire disclosures of which are incorporated herein by reference.

In the embodiment of FIGS. 4 and 5, the distal end of the flexible tubing 19 of the tip section 14 receives a stem 43 of a notched proximal end of the tip electrode. Polyurethane glue or other adhesive may be used to secure the interface between the tip section 14 and the tip electrode 38. To further secure the attachment between the tip section 14 and the tip electrode 38, a pocket 47 (shown in broken lines in FIG. 5) can be formed in the proximal end of the tip electrode to receive the distal end of the deflection structure 17. Polyurethane glue or other suitable adhesives may be used to bond the distal end of the structure in the pocket.

As shown in the embodiment of FIG. 6, the lumens 23 and 25 carrying the puller wires 32 lie about 180 degrees apart from each other along a diameter that is generally perpendicular to the plane of the deflection mechanism 17. As such, the puller wires work in cooperation with the deflection mechanism to deflect the tip section in-plane. This arrangement advantageously reduces twisting of the tip section during deflection.

The deflection mechanism 17 also acts to increase the lateral tip stability, which results in the user being able to create a greater contact force against the heart tissue. As a result of the inventive design, when heart tissue exerts a force against a proximal portion of the tip section 14, the distal portion of the tip section 14 will not deflect away from the heart tissue, but instead be forced back toward the tissue due to the strip 17.

Figure 7:
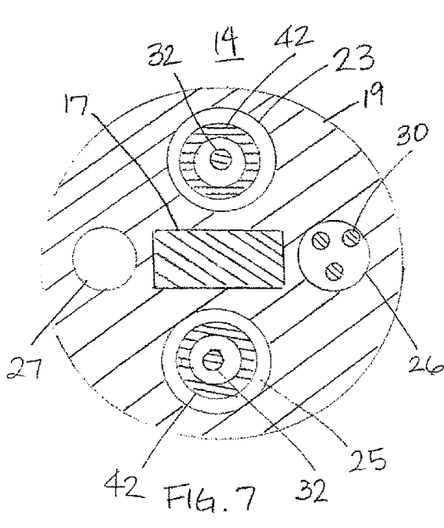
FIG. 7 is a traverse cross-sectional view of another embodiment of the tip section with a deflection mechanism.
Figure 7A:
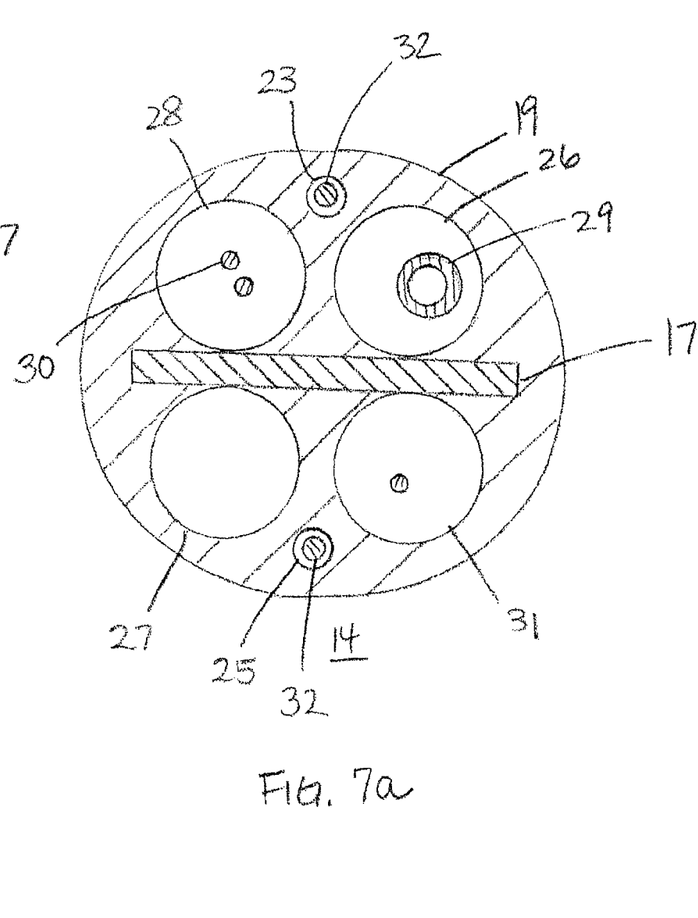
FIG. 7a is a traverse cross-sectional view of a particularly preferred embodiment of the tip section with a deflection mechanism.

FIG. 7a illustrates a particularly preferred embodiment of the tip section 14. The tubing 19 has a slightly ovalized cross section (e.g., created from joining two half ellipses) with a dimension of about 0.092 inches and an orthogonal dimension of about 0.087 inches. The deflection mechanism 17 has a width of about 0.072 inches and a thinness of about 0.006 inches. In most instances, the thicker dimension of the deflection mechanism is aligned with the thicker dimension of the tubing 19 and the thinner dimension is aligned with the thinner dimension of the tubing 19 so that the tubing 19 cooperates with the in-plane deflection bias of the deflection mechanism. The puller wire lumens 23 and 25 are on opposite sides of the deflection mechanism 17 across its thinner dimension and the additional lumens 26, 27, 28 and 31 are paired off in diametrically opposing configurations.

Figure 8:
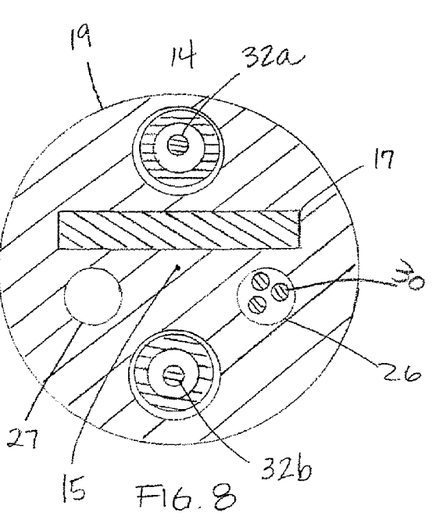
FIG. 8 is a traverse cross-sectional view of another embodiment of the tip section with an off-center deflection mechanism.
Figure 9:
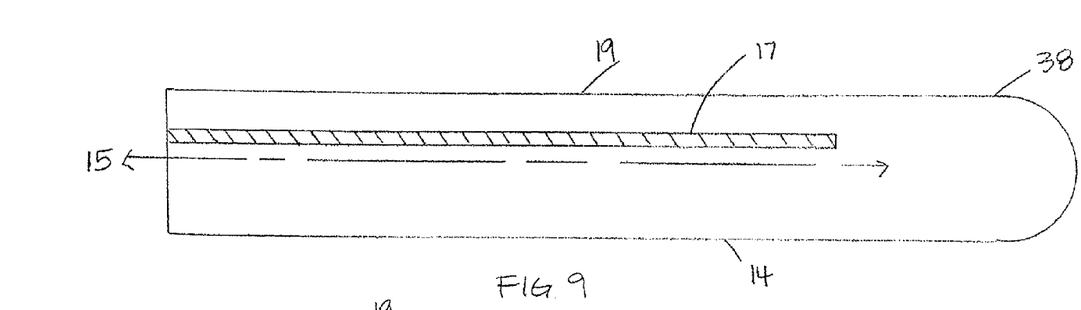
FIG. 9 is a side cross-sectional view of an embodiment of the tip section with an off-center deflection mechanism.

It is understood by one of ordinary skill in the art that the configuration of the deflection mechanism 17 is not limited to that shown in FIGS. 1-6, as discussed further below. As shown in FIG. 7, the additional lumens 26 and 27 can be located along the same diameter as the deflection mechanism 17. Moreover, the mechanism 17 can also be positioned off the centerline 15 as shown in FIGS. 8 and 9 if a different but still in-plane deflection is desired, for example, where the tip section 14 is deflected more readily by an adjacent puller wire 32a than a remote puller 32b (see FIG. 8). In this instance, the additional lumens 26 and 27 are relocated as appropriate or desired.

Figure 10:
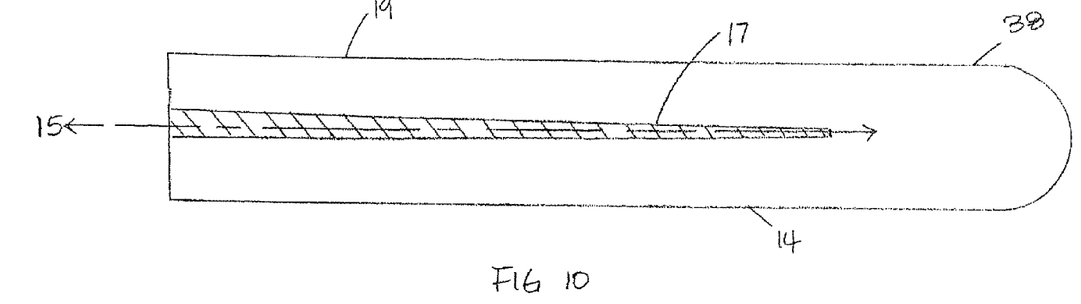
FIG. 10 is a side cross-sectional view of another embodiment of the tip section with a deflection mechanism having a nonuniform cross section.
Figure 11:
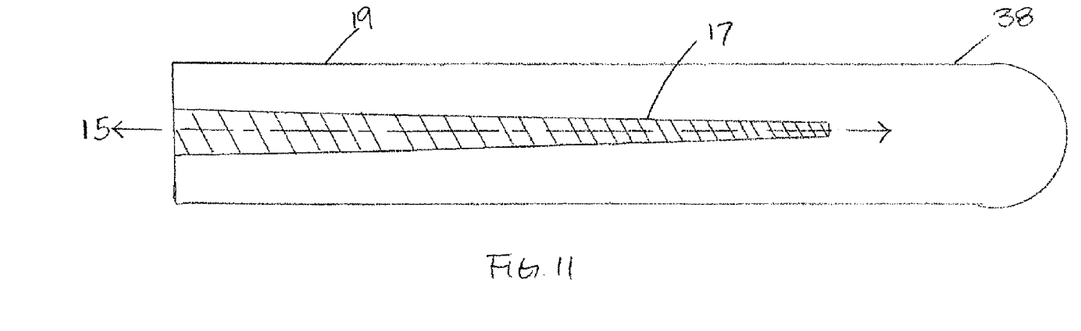
FIG. 11 is a side cross-sectional view of yet another embodiment of the tip section with a deflection mechanism having a nonuniform cross section.

The size of the cross section 21 of the mechanism 17 may be nonuniform along its length. In the embodiment shown in FIGS. 10 and 11, the deflection mechanism is tapered along its length, that is, the rectangular cross-section of the deflection mechanism at the proximal end of the mechanism 17 is greater than at the distal end. Moreover, the increase may be only in half of the cross section, e.g., above the center line 15 as shown in FIG. 10, or in the entirety of the cross section, e.g., above and below the center line 15 as shown in FIG. 11, to further vary the deflection characteristics of the tip section 14.

Figure 12:
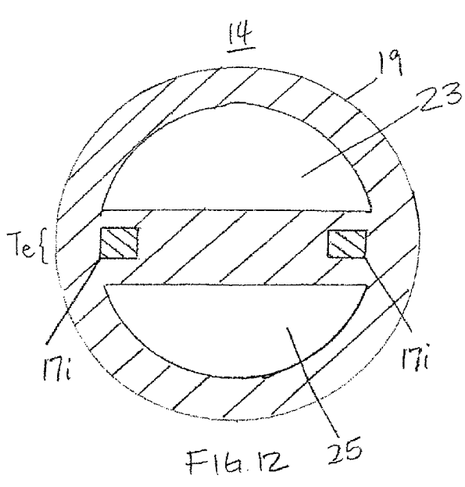
FIG. 12 is a traverse cross-sectional view of another embodiment of the tip section with a deflection mechanism comprising two deflection members and lumens with a semi-circular cross-section.
Figure 13:
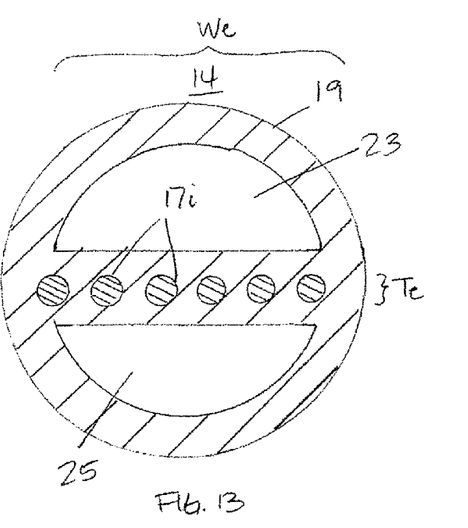
FIG. 13 is a traverse cross-sectional view of another embodiment of the tip section with a deflection mechanism comprising three deflection members.
Figure 14:
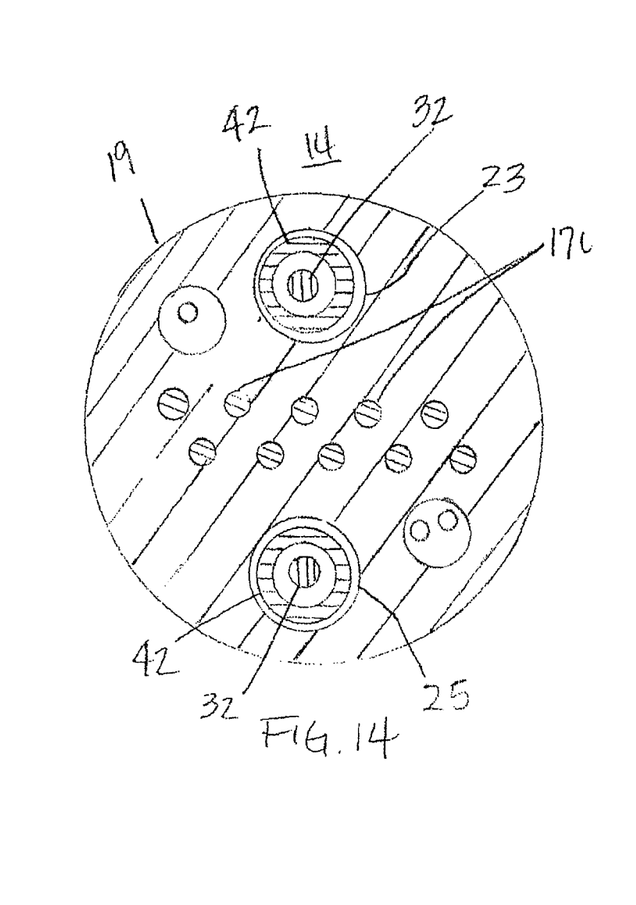
FIG. 14 is a traverse cross-sectional view of another embodiment of the tip section with a deflection mechanism comprising ten deflection members.

In another alternative embodiment, the deflection mechanism 17 comprises multiple members or portions 17$i$, each having a rectangular, square or circular cross-section. As shown in FIGS. 12-14, there may be two or more deflection members 17$i$ that are generally arranged in an N×M array design of N rows by M columns, where N spanning the thickness dimension ranges between 1 and 3 and M spanning the width dimension ranges between 2 and 50.

In the embodiment of FIG. 12, there are two deflection members 17$i$ spanning one row and two columns such that N=1 and M=2, with each deflection member 17$i$ having a rectangular cross section (which can include a square cross-section). In the embodiment of FIG. 13, there are six deflection members 17$i$ spanning one row and six columns such that N=1 and M=6, with each deflection member 17$i$ having a circular cross-section (such as when using conventional wires). In the embodiment of FIG. 14, there are ten deflection members spanning two rows and five columns such that N=2 and M=5, with the columns offset from each other.

For any of the foregoing variations, the tip section remains biased for in-plane deflection so long as the effective or combined area moments of inertia $I_x$ and $I_y$ are unequal. Accordingly, a deflection mechanism comprising multiple deflection members still naturally exhibits a tendency to flex in-plane, that is, to flex in a plane parallel with the mechanism's thinner dimension with the greater area moment of inertia and resist flexure in a plane parallel with the mechanism thicker dimension with the lesser area moment of inertia. It is also understood that the proximal end and the distal end of each deflection member need not be in the same longitudinal position with each other so as to further vary the flexure characteristics of the tip section.

Figure 15:
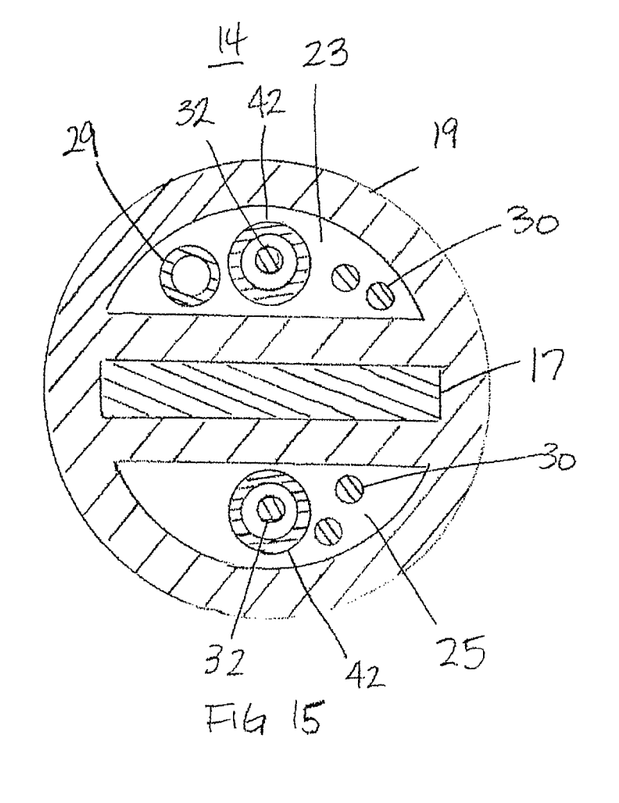
FIG. 15 is a traverse cross-section view of another embodiment of the tip section with a deflection mechanism and lumens with a semi-circular cross section.
Figure 16:
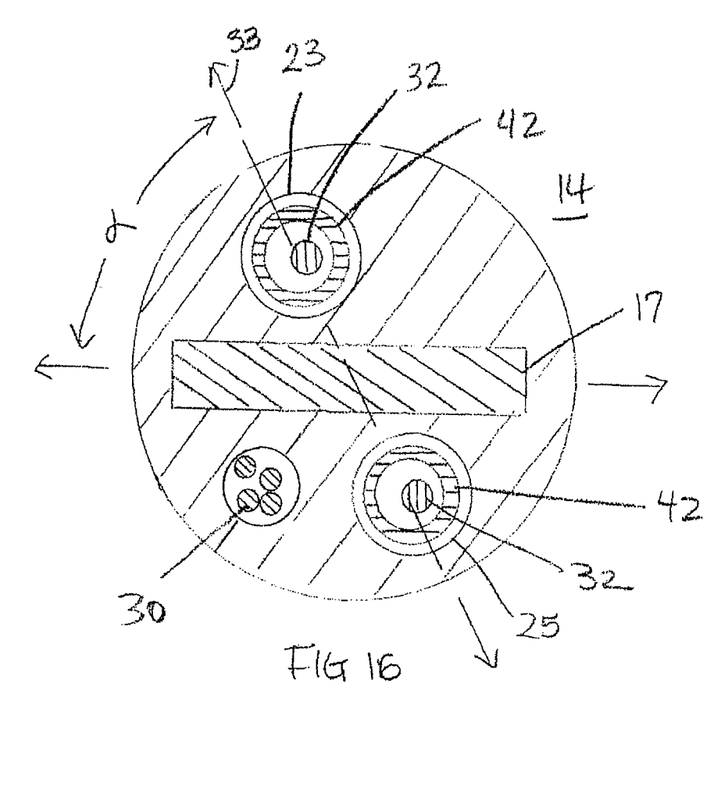
FIG. 16 is a traverse cross-sectional view of another embodiment of the tip section with a deflection mechanism and puller wire lumens defining a nonorthogonal angle therebetween.

In an alternative embodiment, the lumens carrying the puller wires have a noncircular cross-section, as shown in FIGS. 12-13 and 15. In particular, lumens 23 and 25 each have a semi-circular cross-section and can receive other components such as the lead wires 30 and/or the infusion tube 29. Notably, the cross-section of the lumens can be varied as desired or appropriate so long as the deflection mechanism 17 is securely embedded in the tubing 19. For other deflection characteristics as desired or appropriate, the deflection mechanism 17 (whether or not comprising multiple deflection members) and a diameter of the puller wires 32 can be positioned at a nonorthogonal angle to each other. As shown in FIG. 16, an angle α between a diameter 33 along which the puller wires 32 and the plane of the deflection mechanism 17 can be lesser or greater than 90 degrees. In this arrangement and depending on the degree of the angle α, the tip section may exhibit a torsional deflection that combines in-plane and off-plane flexures.

Moreover, the point of attachments of the distal end of the puller wires can be at different locations along the catheter body or tip section with one distal end being more distal than the other distal end, for example, an S-shape deflection, as described in U.S. Pat. No. 6,198,974, the entire disclosure of which is incorporated herein.

The deflection mechanism or members can also be braided or woven, and/or be of a super elastic alloy (with or without temperature-responsiveness) or other spring material which would enable the tip section to spring back to a center/neutral position and improve the tip section response to deflection. The super elastic deflection mechanism could also prevent tip section damage due to buckling or bending and a generally clean tip section profile would be maintained. The tip section can also be pre-formed to facilitate access to certain locations in the heart.

It is further contemplated that the tubing 19 of the tip section 14 can be manufactured in an manner wherein the deflection mechanism or members can be separated from the tubing such that it can be slid distally for removal from the tubing or slid proximally for insertion into the tubing, as desired or appropriate.

Figure 17:
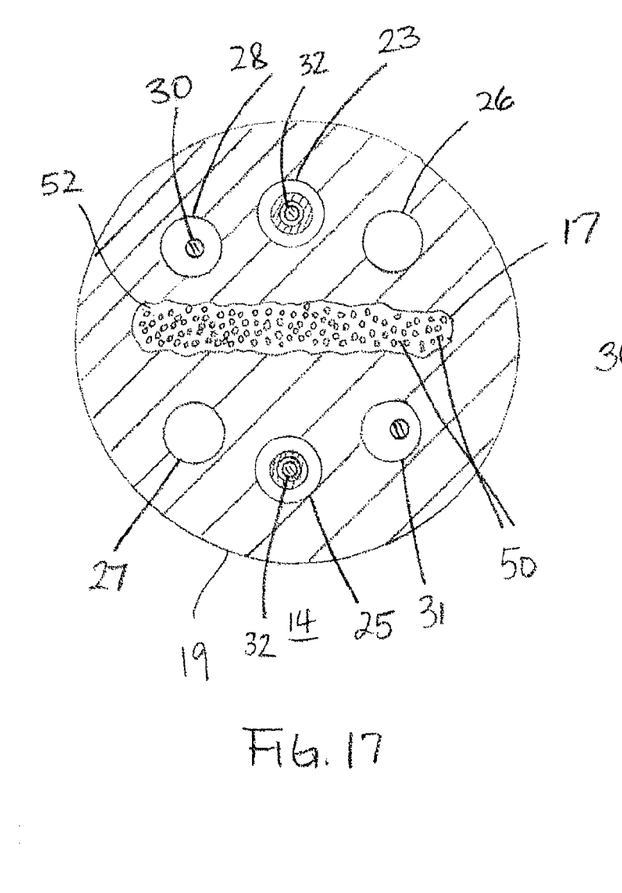
FIG. 17 is a traverse cross-sectional view of another embodiment of the tip section with a deflection mechanism comprising a plurality of engineered structural fibers.

Referring to FIG. 17, the deflection mechanism 17 can also be formed from a multitude of engineered structural fibers 50 that are configured into a structure 52, such as a ribbon, a flat braid, fabric or cloth, as shown in FIG. 17. The structure 52 has an effective cross section with unequal area moments of inertia about two centroidal axes. The tubing 19 of the tip section 14 can be extruded around the member 52 and the mandrels, where only the mandrels are removed to form the lumens of the tip section. In accordance with the present invention, the fibers 50 are arranged to provide an effective thicker dimension along a first centroidal axis and an effective thinner dimension along a second centroidal axis generally orthogonal to the first centroidal axis, with unequal area moments of inertia about the two respective axes, so that the tip section 14 is biased to deflect in a plane parallel with the effective thinner dimension along the second centroidal axis and to resist deflection in a plane parallel with the effective thicker dimension along the first centroidal axis. The fibers may be made of any suitable material, including Kevlar®, Vectran®, carbon fiber or glass.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A steerable catheter comprising:
    an elongated, flexible tubular catheter body having proximal and distal ends and a lumen extending therethrough;
    a tip section at the distal end of the catheter body, the tip section comprising a flexible plastic tubing having a pair of diametrically-opposed lumens extending therethrough;
    a control handle at the proximal end of the catheter body;
    first and second puller wires, each extending through one of the pair of lumens in the tip section and through the lumen of the catheter body, each having a proximal end anchored to the control handle and a distal end anchored to the tip section, whereby the puller wires are longitudinally moveable relative to the catheter body to cause deflection of the tip section; and
    an elongated deflection mechanism extending in the tip section without contacting the first and second puller wires, the deflection mechanism being configured to provide the tip section with in-plane deflection and comprising a plurality of deflection members, wherein either one of the plurality of deflection members has a proximal end at a different location than a proximal end of another of the plurality of deflection members or one of the plurality of deflection members has a distal end at a different location than a distal end of another of the plurality of deflection members.

2. A catheter of claim 1, wherein the deflection mechanism comprises a first centroidal axis and a second centroidal axis and is configured to define a lesser area moment of inertia about the first centroidal axis and a greater area moment of inertia about the second centroidal axis, the deflection mechanism being configured to bias the tip section to flex in a plane parallel with the second centroidal axis with the greater area moment of inertia.

3. A catheter of claim 1, wherein the deflection mechanism comprises a first centroidal axis and a second centroidal axis and is configured to define a lesser area moment of inertia about the first centroidal axis and a greater area moment of inertia about the second centroidal axis, wherein the first and the second centroidal axes are generally orthogonal to each other.

4. A steerable catheter comprising:
    an elongated, flexible tubular catheter body having proximal and distal ends and a lumen extending therethrough;
    a tip section at the distal end of the catheter body, the tip section comprising a flexible plastic tubing having a pair of diametrically-opposed lumens extending therethrough;
    a control handle at the proximal end of the catheter body;
    first and second puller wires, each extending through one of the pair of lumens in the tip section and through the lumen of the catheter body, each having a proximal end anchored to the control handle and a distal end anchored to the tip section, whereby the puller wires are longitudinally moveable relative to the catheter body to cause deflection of the tip section; and
    a deflection mechanism generally extending longitudinally along a centerline of the tip section and situated between the first and second puller wires without contacting the first and second puller wires, the mechanism having a thicker dimension and a thinner dimension so as to bias the tip section to deflect in a plane parallel with the thinner dimension and resist deflection in a plane parallel with the thicker dimension, wherein the deflection mechanism has a cross-section that decreases along the length of the deflection mechanism from the proximal end to the distal end.

5. A catheter according to claim 4, wherein the deflection mechanism has a cross section defined by W and T where W is the thicker dimension and, T is the thinner dimension and W=nT with n ranging between about 2 and 20.

6. A catheter according to claim 4, wherein the cross-section is rectangular.

7. A catheter according to claim 4, wherein the deflection mechanism is positioned along a centerline of the tip section.

8. A catheter according to claim 1, wherein the plurality of deflection members are arranged in an array of N rows by M columns.

9. A catheter according to claim 8, wherein N=1 and M ranges between 2 and 50.

10. A catheter according to claim 8, wherein N=2 and M ranges between 3 and 10.

11. A catheter according to claim 8, wherein the columns are offset.

12. A catheter according to claim 4, further comprising a tip electrode at the distal end of the tip section.

13. A catheter according to claim 12, wherein a distal end of the deflection mechanism extends into the tip electrode.

14. A catheter according to claim 1, further comprising an infusion tube extending through the catheter body and a third lumen through the tip section.

15. A catheter according to claim 1, wherein the first and second lumens each have a generally circular cross section.

\* \* \* \* \*